(12) United States Patent
Saito (10) Patent No.: US 9,913,660 B2
(45) Date of Patent: *Mar. 13, 2018

(54) MEDICAL KNIFE

(71) Applicant: MANI, Inc., Utsunomiya, Tochigi (JP)

(72) Inventor: Masahiko Saito, Tochigi (JP)

(73) Assignee: MANI, Inc., Utsunomiya, Tochigi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/087,587

(22) Filed: Mar. 31, 2016

(65) Prior Publication Data

US 2016/0228142 A1 Aug. 11, 2016

Related U.S. Application Data

(63) Continuation of application No. 13/142,416, filed as application No. PCT/JP2009/071269 on Dec. 22, 2009, now Pat. No. 9,381,117.

(30) Foreign Application Priority Data

Dec. 26, 2008 (JP) .................................. 2008-332307

(51) Int. Cl.
*A61B 17/32* (2006.01)
*A61B 17/3209* (2006.01)
(Continued)

(52) U.S. Cl.
CPC ...... *A61B 17/3209* (2013.01); *A61B 17/3205* (2013.01); *A61B 17/3211* (2013.01);
(Continued)

(58) Field of Classification Search
CPC .......... A61B 17/3211; A61B 17/32093; A61B 17/32; A61F 9/0133
See application file for complete search history.

(56) References Cited

U.S. PATENT DOCUMENTS 4,585,446 A * 4/1986 Kempf .................. A61M 5/158
604/117
4,742,637 A 5/1988 Musacchia .......................... 43/6
(Continued)

FOREIGN PATENT DOCUMENTS

JP 2001-238890 A 9/2001
JP 2005-013379 A 1/2005
(Continued)

OTHER PUBLICATIONS

International Search Report for PCT/JP2009/071269, Apr. 6, 2010, (6 pages).

*Primary Examiner* — Julie A Szpira
(74) *Attorney, Agent, or Firm* — Shlesinger, Arkwright & Garvey LLP (57) ABSTRACT

A medical knife which maintains low penetration resistance, without the maximum-width parts of the medical knife creating sudden changes in penetration resistance even when passing through tissue. Knife includes a pointed tip, a cutting part which has edges having first oblique faces which are formed along the outer periphery, and second oblique faces which are formed inside the first oblique faces. Maximum-width parts are formed contiguously with the cutting part. A shank part is formed contiguously with the maximum-width parts. The cutting part is formed in such a way that the shape of the planar projection thereof becomes wider from the pointed tip towards the maximum-width parts, and the first oblique faces extend further towards the shank part side than the second oblique faces over at least one portion of the area running from the maximum-width parts to the shank part.

4 Claims, 4 Drawing Sheets

(51) Int. Cl.
*A61B 17/3211* (2006.01)
*A61F 9/013* (2006.01)
*A61B 17/3205* (2006.01)
*A61F 9/007* (2006.01)

(52) U.S. Cl.
CPC ........ *A61F 9/0133* (2013.01); *A61B 2218/00* (2013.01); *A61F 9/00736* (2013.01)

(56) References Cited

U.S. PATENT DOCUMENTS

| | | | |
|---|---|---|---|
| 5,044,640 A | 9/1991 | DelMonte et al. | 473/584 |
| 5,350,393 A * | 9/1994 | Yoon | A61B 10/0233 |
| | | | 604/164.12 |
| 5,545,150 A | 8/1996 | Danks et al. | 604/256 |
| 5,713,915 A * | 2/1998 | Van Heugten | A61F 9/0133 |
| | | | 606/166 |
| 6,063,099 A * | 5/2000 | Danks | A61B 17/3496 |
| | | | 604/264 |
| 6,554,840 B2 * | 4/2003 | Matsutani | A61F 9/0133 |
| | | | 606/107 |
| D535,747 S * | 1/2007 | Isogimi | A61F 9/0133 |
| | | | D24/146 |
| 7,648,516 B2 * | 1/2010 | Matsutani | A61B 17/3211 |
| | | | 606/166 |
| 2001/0029386 A1 | 10/2001 | Matsutani et al. | |
| 2005/0004587 A1 | 1/2005 | Matsutani et al. | |
| 2005/0004588 A1 | 1/2005 | Saito et al. | |
| 2005/0070941 A1 * | 3/2005 | Isogimi | A61F 9/0133 |
| | | | 606/166 |
| 2006/0058824 A1 * | 3/2006 | Kozlowski | A61F 9/0133 |
| | | | 606/167 |
| 2006/0217750 A1 | 9/2006 | Ghannoum | |
| 2007/0005087 A1 * | 1/2007 | Smith | A61B 17/3417 |
| | | | 606/185 |

FOREIGN PATENT DOCUMENTS

| | | |
|---|---|---|
| JP | 2005-103035 A | 4/2005 |
| JP | 4161026 B2 | 10/2008 |

* cited by examiner

MEDICAL KNIFE

CROSS REFERENCE TO RELATED APPLICATIONS

This application is a continuation of application Ser. No. 13/142,416, filed Jun. 27, 2011, which is a National Stage application of International Application No. PCT/JP2009/071269, filed Dec. 22, 2009, which claims the priority of Japanese application No. 2008-332307, filed Dec. 26, 2008, and each of which is incorporated herein by reference.

FIELD OF THE INVENTION

The present invention relates to a medical knife capable of making an incision with small penetration resistance, which does not generate drastic change in the penetration resistance even when a maximum-width part passes, when incising an affected area.

In a cataract operation, a cornea and a sclera are incised with a width corresponding to a dimension of a lens to be embedded for embedding the lens in an eyeball. As the medical knife used when incising the eyeball, there is one of which planar shape is formed into a substantially rhombic shape. Such medical knife has a sharp tip, a cutting part having two edges radially formed from the tip, a maximum-width part in which a width dimension of the cutting part is the largest, and a shank part continuously formed from the maximum-width part of which width dimension decreases as is away from the maximum-width part (for example, refer to Patent Document 1).

In a case of the above-described medical knife, by allowing the same to straightly penetrate the eyeball, an incision corresponding to the dimension of the maximum-width part may be formed. Especially, in the medical knife disclosed in Patent Document 1, durability of the sharp tip may be improved, and since the edges are formed on both sides from the maximum-width part to the shank part, the penetration resistance may be made small.

In the medical knife disclosed in Patent Document 1, the edges are formed on the both sides in the maximum-width part and the edges are formed also from the maximum-width part to the shank part. Therefore, high incision performance to the tissue is maintained of course from the tip to the maximum-width part and even after the maximum-width part passes through the tissue.

Therefore, the penetration resistance generated when incising the eyeball with the above-described medical knife is a substantially similar small value from the tip to the maximum-width part and the substantially similar penetration resistance is maintained even after the maximum-width part passes through the tissue. When the maximum-width part passes through the tissue and the width of the knife decreases toward the shank, the penetration resistance drastically decreases.

Patent Document 1: Japanese Patent No. 4161026

DISCLOSURE OF INVENTION

Problem to be Solved by the Invention

When incising the eyeball with the medical knife, a part with the largest resistance is the cornea and the sclera, and the resistance in a crystal lens is small. That is to say, when performing incision operation by allowing the sharp tip of the medical knife to face the tissue, the penetration resistance drastically increases to achieve the largest value at a stage in which the tip penetrates the tissue to form the initial incision. Thereafter, the penetration resistance is generated also when the edge continuous from the sharp tip expands the tissue. Then, after the maximum-width part passes through the tissue, the penetration resistance decreases. In this manner, when making an incision with the medical knife, the penetration resistance changes in accordance with progress in incision.

The change in the penetration resistance is preferably small. For example, when the change between the penetration resistance when forming the initial incision to the tissue and the penetration resistance when expanding the initial incision is drastic and large, since a doctor handles the medical knife by applying force necessary to form the initial incision, excessive force acts on the tissue from a moment that the initial incision is formed and a penetration speed might increase to cause excessive incision. Also, when the maximum-width part of the medical knife passes through the tissue, when the change between the penetration resistance when expanding the initial incision and the penetration resistance after the maximum-width part passes through the tissue is drastic and large, since the doctor handles the medical knife by applying force necessary to expand the tissue, the excessive force acts on the tissue from a moment that the maximum-width part passes through the tissue and the penetration speed might increase to cause the excessive incision.

Therefore, it is required that the doctor who handles the medical knife sensitively responds to slight change in the penetration resistance sensed by hand and finger, so that delicate handling and sensitive sense are required for recognizing the change in the penetration resistance, and there is a problem of fatigue in an operation.

An object of the present invention is to provide the medical knife capable of maintaining the small penetration resistance, not generating the drastic change in the penetration resistance even when the maximum-width part passes through the tissue, and improving handleability.

Means for Solving Problem

In order to solve the above-described problem, the medical knife according to the present invention includes a sharp tip, a cutting part including an edge formed of a first oblique face formed along an outer periphery and a second oblique face formed inside the first oblique face, a maximum-width part formed continuously from the cutting part, and a shank part formed continuously from the maximum-width part, wherein a planar projection shape of the cutting part is formed such that a width dimension increases from a side of the sharp tip toward the maximum-width part, and the first oblique face extends further toward a side of the shank part than the second oblique face on at least a part of a portion from the maximum-width part to the shank part side.

Effect of the Invention

In the above-described medical knife (hereinafter, simply referred to as the "knife"), the penetration resistance generated when incising the tissue may be maintained small and the penetration resistance does not drastically change even when the maximum-width part passes through the tissue. Therefore, the doctor may make weight on sensitivity to application of the force small when handling to reduce the fatigue.

That is to say, in the knife of the present invention, in the planar shape (planar projection shape), the width dimension increases from the sharp tip to the maximum-width part and the shank part is formed continuously from the maximum-width part. Also, the cutting part has the edge formed of the first oblique face and the second oblique face formed inside the first oblique face. The first oblique face extends further toward the shank part side than the second oblique face on at least a part of the portion from the maximum-width part to the shank part.

In the knife of the present invention configured as above, in the planar shape in the maximum-width part, the first oblique face to form the edge obliquely intersects with the maximum-width part of the knife and the first oblique face is formed along an outer periphery of the maximum-width part to the shank part side. Therefore, a substantially triangle wedge-shaped surface having an intersection with the edge as an apex and is defined by an end edge of the first oblique face and an end edge of a lower oblique face of which area increases from the edge side toward the shank part side is formed on a side surface of the knife.

Also, since the first oblique face is formed so as to be overlapped with the second oblique face on at least a part of the portion from the maximum-width part to the shank part side, when it is configured such that the width dimension gradually decreases from the maximum-width part toward the shank part, a cross-sectional area from the maximum-width part on which the first and second oblique faces are formed to the shank part side may be made substantially constant.

Therefore, the knife of the present invention may maintain the penetration resistance small because the edge is formed on the portion from the sharp tip to the maximum-width part, and may maintain the small penetration resistance after forming the initial incision to the tissue to the maximum-width part because the edges are formed on the both sides of the maximum-width part.

After the maximum-width part of the knife passes through the tissue by further handling of the knife, the edges are not formed on the both sides of the knife, so that the penetration resistance larger than the penetration resistance generated when the edge passes through the tissue is generated. At that time, since a shape of the side surface of the maximum-width part of the knife is the substantially wedge-shape, this acts in a direction in which the penetration resistance increases together with increase in the penetration, on the other hand, the first oblique face is formed so as to be overlapped with the second oblique face at least a part of the portion from the maximum-width part to the shank part side and the width dimension decreases, and this acts in the direction in which the penetration resistance decreases, so that the generated penetration resistance becomes substantially constant in the vicinity of the maximum-width part. At the same time, after the maximum-width part passes through the tissue, the width of the knife decreases, so that this decreases together with this.

Therefore, the penetration resistance is continuously generated also after the maximum-width part of the knife passes through the tissue and the doctor is not affected by the drastic change in the penetration resistance. Therefore, the doctor may recognize the change in the penetration resistance while handling the knife, thereby recognizing that the incision of the tissue is completed. Also, since the drastic change in the penetration resistance is not generated, there is a little possibility of forming the excessive incision due to too much force applied when the maximum-width part passes and it is possible to make the weight on the sensitivity to the application of the force small.

DESCRIPTION OF LETTERS OR NUMERALS

| A | knife |
| --- | --- |
| 1 | cutting part |
| 2 | maximum-width part |
| 3 | shank part |
| 4 | tip |
| 5 | edge |
| 6 | first oblique face |
| 7 | lower oblique face |
| 8 | second oblique face |
| 9 | upper flat surface |
| 6a, 8a | boundary line |
| 10 | lower flat surface |
| 11 | side surface |

BEST MODE(S) FOR CARRYING OUT THE INVENTION

Figure 1:
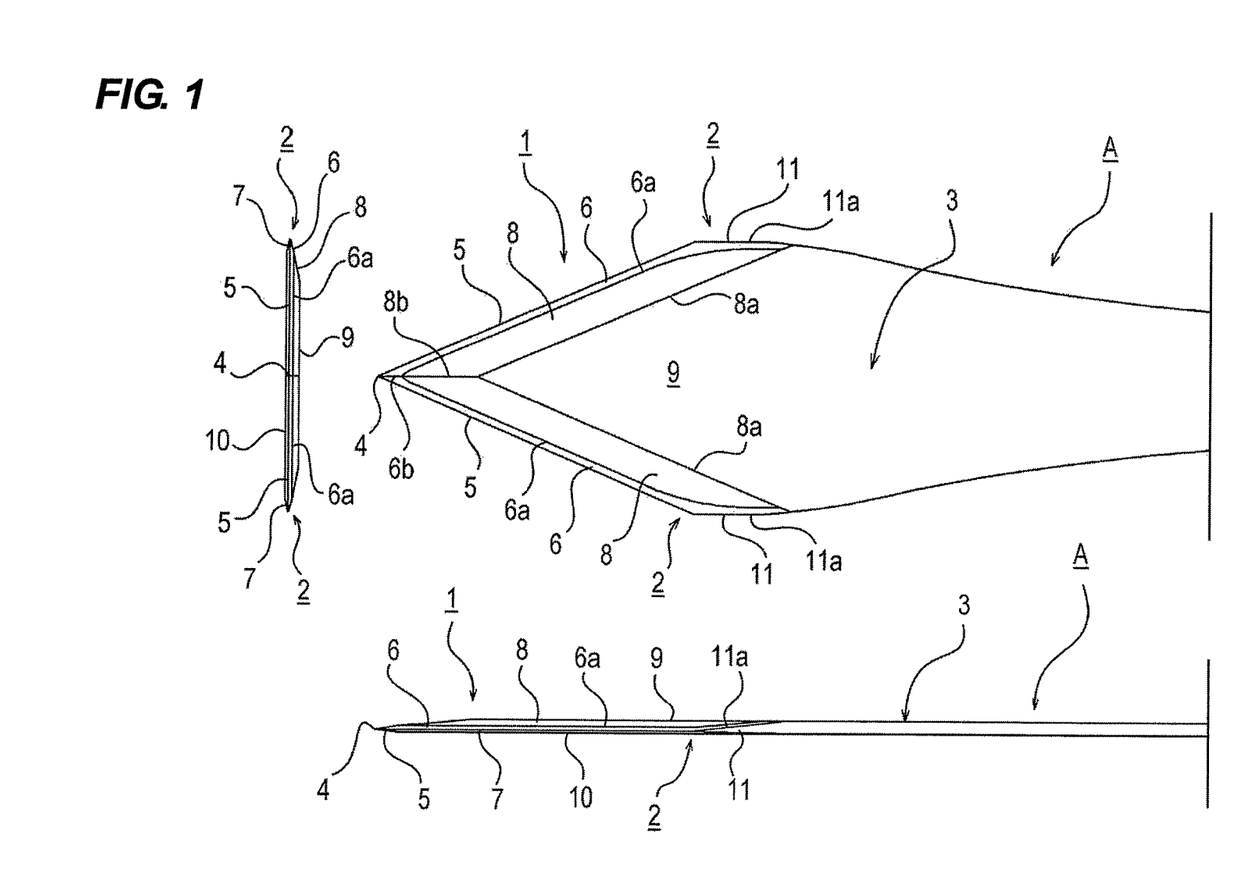
FIG. 1 is an orthographic view of a knife according to this embodiment.
Figure 2:
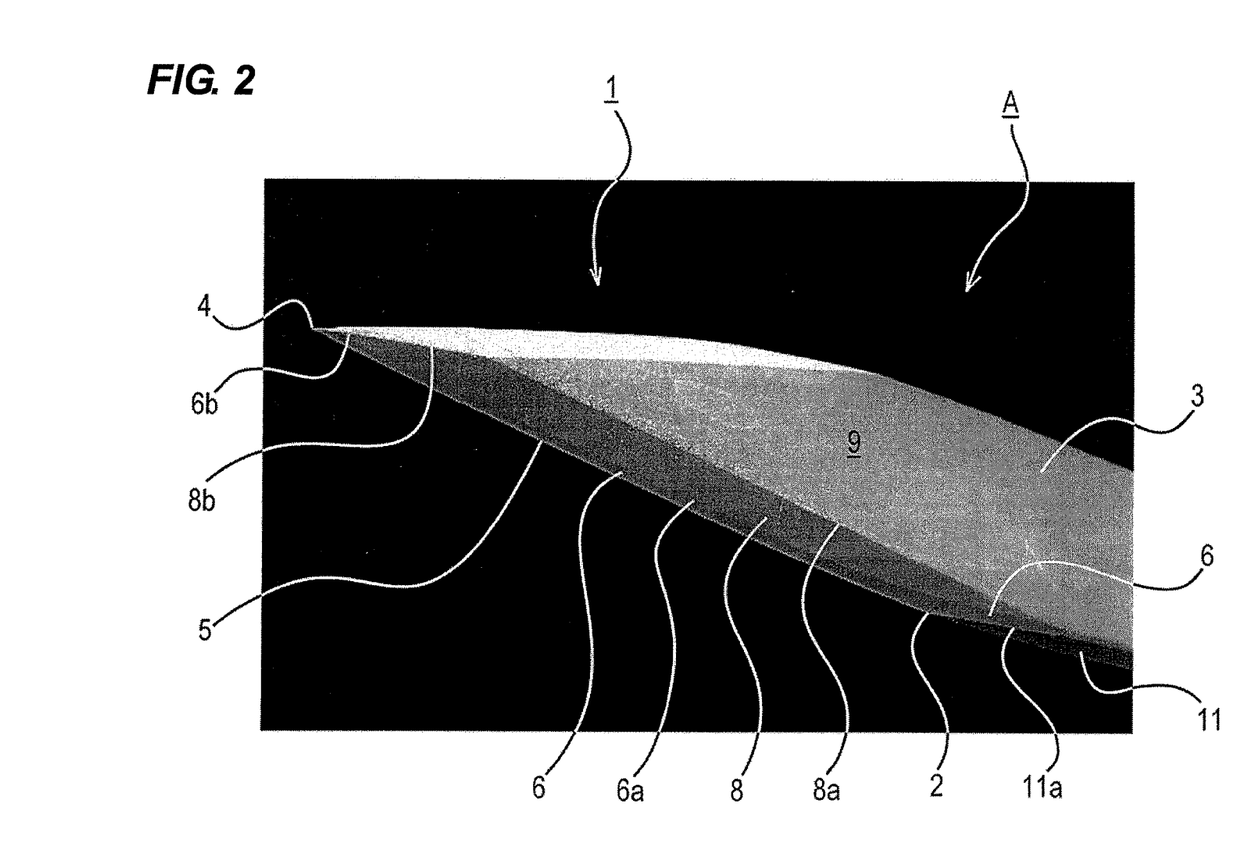
FIG. 2 is a perspective view of the knife.

Hereinafter, a preferred embodiment of a medical knife according to the present invention is described with reference to the drawings. FIG. 1 is an orthographic view of the knife according to this embodiment. FIG. 2 is a perspective view of the knife.

The knife according to the present invention has a function to penetrate a tissue of an eyeball and the like to form an initial incision and make an incision in a width direction from the initial incision as a starting point to expand the same in a thickness direction. Especially, it is configured such that drastic difference is not generated between penetration resistance generated when the knife penetrates the tissue to incise and the penetration resistance just after a maximum-width part of the knife passes through the tissue.

A material to form the knife according to the present invention is not especially limited, and steels such as stainless steel and carbon steel may be used. However, in view of an antirust property and easier working, the stainless steel is preferably used and among others, austenitic stainless steel is desirably used.

When the austenitic stainless steel is used as the material, it is preferable to apply cold plastic working at a predetermined working rate to extend a structure in a fiber shape and apply press working, polish working and another necessary working while maintaining the fiber-shaped structure in order to increase hardness of the material.

In FIGS. 1 and 2, a knife A is composed of a cutting part 1, a maximum-width part 2 on a widest position of the cutting part 1, and a shank part 3 formed continuously from the maximum-width part 2. A tip of the cutting part 1 is formed as a sharp tip 4 and edges 5 are formed on both sides from the tip 4 as the starting point toward the maximum-width parts 2. Also, it is formed such that a width dimension gradually decreases from the maximum-width part 2 toward the shank part 3. Therefore, a planar shape (planar projection shape) from the cutting part 1 through the maximum-width part 2 to the shank part 3 of the knife A is formed into a substantially rhombic shape.

Detailed dimensions such as a length dimension from the tip 4 to the maximum-width part 2 and the width dimension of the maximum-width part 2 are variously set according to an object of the knife A, for example, a specification such as a dimension of the incision.

Also, the planar shape of the maximum-width part 2 is not especially limited, the knife A may have a rhombic planar shape with the maximum-width parts 2 as apices and the maximum-width part 2 may be slightly linearly formed in a longitudinal direction of the knife A.

The edge 5 is formed along an outer periphery of the cutting part 1. The edge 5 has a function to incise the tissue including a cornea and a sclera and is formed of first oblique face 6 formed on an upper side of a plane including two edges 5 formed on the both sides from the tip 4 to the maximum-width part 2 as a boundary and a lower oblique face 7 formed on a lower side thereof intersecting with each other. In this manner, since the first oblique face 6 and the lower oblique face 7 form the edge 5 together, the oblique faces 6 and 7 are formed as ground surfaces with high smoothness.

A second oblique face 8 is formed inside the first oblique face 6 along the first oblique face 6 formed on the upper side of the edge 5 of the cutting part 1, and a boundary line 6a is formed on a boundary between the both oblique faces 6 and 8. Since the second oblique face 8 does not have a function to form the edge 5, it is not necessarily required to form the same of the ground surface with the high smoothness and this may be a pressed surface or a roughly ground surface. Also, an upper flat surface 9 is formed along the second oblique face 8 and the upper flat surface 9 also may be the pressed surface or the roughly ground surface as the second oblique face 8.

A lower flat surface 10 is formed continuously from the lower oblique face 1 formed on the lower side of the edge of the cutting part 1. Since the lower flat surface 10 is formed as a surface, which does not have the function to form the edge 5, it is not necessarily required to form the same of the ground surface with the high smoothness and this may be formed as the roughly ground surface or the pressed surface.

In the cutting part 1, the first oblique face 6 is formed of a flat surface and this is formed to have the same width (dimension from the edge 5 to the boundary line 6a) from the tip 4 to the vicinity of the maximum-width part 2. The lower oblique face 7 formed on the lower side of the plane including the two edges 5 also is formed as the flat surface. Therefore, the edge 5 has a pointed sharp shape by intersection of the two flat surfaces. In such cutting part 1, the boundary line 6a being the boundary between the first oblique face 6 and the second oblique face 8 is formed as a well-defined ridge.

The above-described first oblique face 6 and lower oblique face 7 may be formed by using a grinding material having high flatness and moderate rigidity. As such grinding material, there are a grindstone, a belt-shaped grindstone of which rear surface is supported by a highly rigid frame and the like, and they may be selectively used.

The second oblique face 8 is formed inside the first oblique face 6 along the first oblique face 6. The second oblique face 8 is formed such that an angle relative to the plane including the two edges 5 is smaller than an angle of the first oblique face 6. The second oblique face 8 is substantially linearly formed along the first oblique face 6 through the maximum-width part 2 to a side surface to reach the shank part 3. Thus, a boundary line 8a being a boundary between the second oblique face 8 and the upper flat surface 9 is formed as a well-defined linear ridge.

The two edges 5 are formed from the tip 4 as the starting point, the first oblique faces 6 are formed along the edges 5, and further the second oblique faces 8 are formed inside the first oblique faces 6 along the same, so that a line 6b on which the two first oblique faces 6 intersect with each other and a line 8b on which the two second oblique faces 8 intersect with each other become continuous straight lines beginning from the tip 4.

The first oblique face 6 extends further toward a shank part 3 side than the second oblique face at least a part of a portion from the maximum-width part 2 to the shank part 3 side. In this embodiment, the first oblique face 6 is formed on an outer peripheral side of the second oblique face 8 on a portion from the cutting part 1 through the maximum-width part 2 to the shank 3 of the knife A.

Therefore, the first oblique face 6 extends further toward the shank part 3 side than the second oblique face 8 on the portion from the maximum-width part 2 to the shank part 3. However, it is not required that the first oblique face 6 is formed over an entire length of the second oblique face 8 formed from the maximum-width part 2 to the shank part 3 and this may be formed on a part thereof.

As described above, the knife A is such that the first oblique face 6, the second oblique face 8, and the upper flat surface 9 are formed on the upper side of the plane including the two edges 5 of the cutting part 1, and the lower oblique face 7 and the lower flat surface 10 are formed on the lower side thereof. Therefore, as a shape in a side view of the knife A, the edge 5, the ridge 6a, the upper flat surface 9, and the lower flat surface 10 are represented in a part corresponding to the cutting part 1.

Also, in a side view of the vicinity of the maximum-width part 2 of the knife A, a point on which the edge intersects with the maximum-width part 2 is made an apex, the first oblique face 6 and the lower oblique face 7 form two sides away from each other toward the shank part 3 side, and a triangle-shaped side surface 11 by a line on which the first oblique face 6 intersects with the upper flat surface 9 and a line on which the lower oblique face 7 intersects with the lower flat surface 10 is formed.

On the side surface 11, a corner on the lower side forms an obtuse ridge formed by intersection of the lower oblique face 7, and a corner on the upper side forms an obtuse ridge 11a formed by intersection of the first oblique face 6. Especially, an angle formed by the ridge 11a on the upper side of the side surface 11 (angle between the first oblique face 6 and the side surface 11) becomes larger than the angle formed when the second oblique face 8 directly intersects with the side surface 11, and it is possible to significantly decrease the function to incise the tissue. That is to say, the first oblique face 6 further chamfers a corner portion on which the side surface 11 and the second oblique face 8 intersect with each other, and the ridge 11a on the upper side of the side surface 11 is formed with the large angle.

In this manner, the first oblique face 6 further extending further toward the shank part 3 side than the second oblique face 8 from the maximum-width part 2 to the shank part 3 does not intersect with the lower oblique face 7 but intersects with the side surface 11. Therefore, the edge is not formed on an outer peripheral portion of the first oblique face 6 extending from the maximum-width part 2 to the shank part 3 side.

The knife A composed as above has an excellent incision performance to the tissue by the sharp tip 4 and the edge 5 in the cutting part 1 from the tip 4 to the maximum-width part 2 and is able to decrease the penetration resistance when incising the tissue. Also, the maximum-width part 2 has the incision performance only on an apex portion on which the edge intersects with the side surface 11. However, the edge 5 disappears at the same time as passing through the maximum-width part 2, and further a thickness of the both end portions in the width direction of the knife A increases together with the triangle on the side surface 11, so that resistance (frictional resistance) to expand an incision site is generated when passing through the tissue. Further, since the width dimension of the knife A decreases at the same time as passing through the maximum-width part 2, the side surface 11 is separated from the tissue and the resistance when passing through the tissue decreases.

Therefore, until the maximum-width part 2 of the knife A passes through the tissue, the resistance when the edge incises the tissue is generated as the penetration resistance, and soon after the maximum-width part 2 passes through the tissue, difference between the resistance generated when expanding the tissue and decrease in the resistance by separation of the side surface 11 from the tissue is generated on the maximum-width part as the penetration resistance. That is to say, after the maximum-width part 2 of the knife A passes through the tissue, the penetration resistance does not drastically decrease but gradually changes. Therefore, a doctor may easily recognize that the maximum-width part 2 passes through the tissue and may surely handle with modulation.

Next, a process to manufacture the knife A in which the first oblique face 6 extends further toward the shank part 3 side than the second oblique face 2 in at least a part of the portion from the maximum-width part 2 to the shank 3 side as described above is simply described.

First, a material corresponding to the planar shape of a destination knife A is formed. In this case, when the material is the steel or martensite stainless steel, it is sufficient to cut out a flat plate with the thickness of the knife A into the rhombic shape by pressing. Also, when the material is the austenitic stainless steel and the like, the press working may be applied to a line material having the structure to which cold withdrawing working is applied in advance to be extended in the fiber shape to form the same into a rhombic flat plate shape.

The second oblique face 8 is formed on the rhombic material formed in the above-described manner by pressing or grinding, and thereafter, by forming the first oblique face 6 on a portion from the tip 4 through the maximum-width part 2 to the shank part 3 side by grinding the outer peripheral side of the second oblique face 8, it is possible to extend the first oblique face 6 further toward the shank part 3 side than the second oblique face on at least a part of the portion from the maximum-width part 2 to the shank part 3 side.

Then, the knife A may be manufactured through another process including a predetermined polishing process after forming the lower oblique face 7.

When forming the first oblique face 6 on the rhombic material, by grinding along the edge 5 and thereafter grinding along the side surface 11 from the maximum-width part 2 to the shank part 3 side by changing an attitude of the material, it is possible to extend the first oblique face further toward the shank part 3 side than the second oblique face on a part of the portion from the maximum-width part 2 to the shank part 3 side.

However, it is preferable to continuously perform the grinding along the edge 5 and the grinding along the side surface 11 without performing such grinding in two steps. In this case, the attitude of the material may be continuously changed according to the grinding corresponding to the edge 5 and the grinding corresponding to the side surface 11. When performing such grinding, in the vicinity of the maximum-width part 2 of the knife A, the boundary line 6a between the first oblique face 6 and the second oblique face 8 becomes a curved-line shape and the width of the first oblique face 6 (dimension from the edge 5 to the boundary line 6a and dimension from the side surface 11 to the boundary line 6a) increases.

It is also possible to form the first oblique face 6 in a precedent process and form the second oblique face 8 in a successive process.

Figure 3:
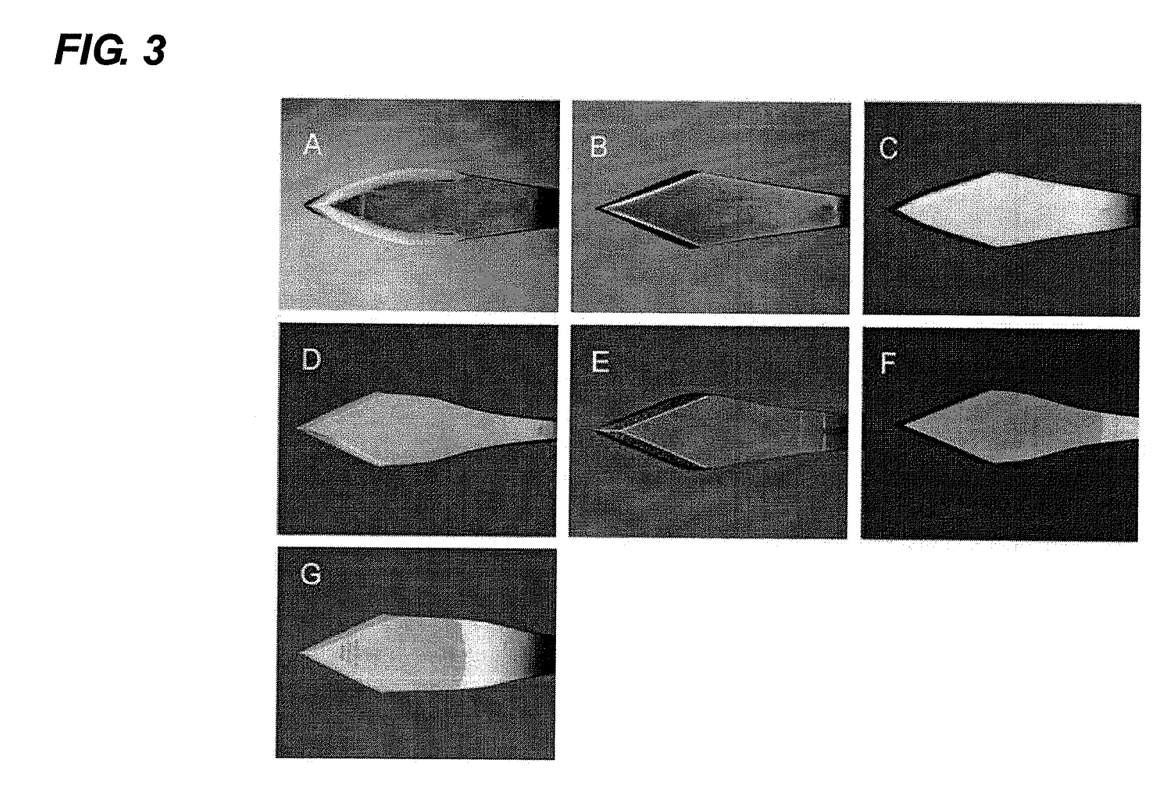
FIG. 3 is plan views of knives of comparative examples A to D, F and G and the knife of the present invention E.
Figure 4:
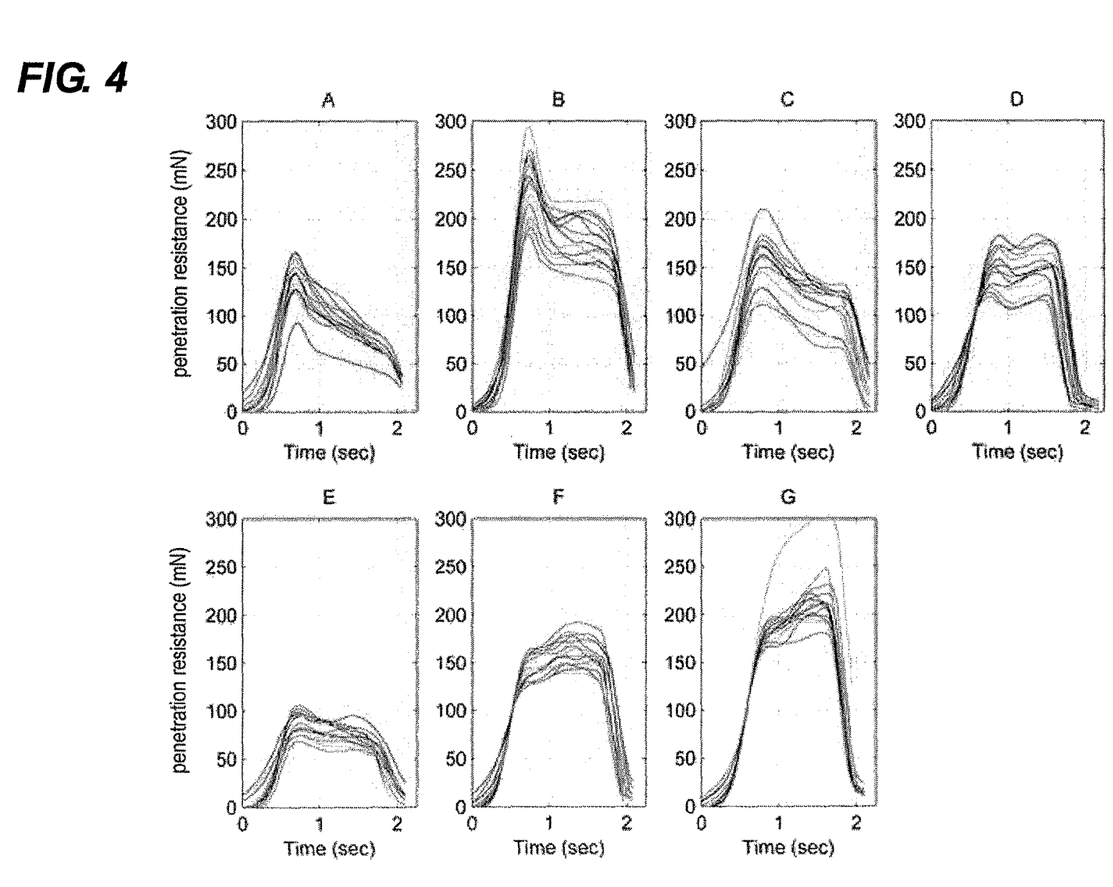
FIG. 4 is views illustrating measured values of penetration resistance by the knives of the comparative examples A to D, F and G and the knife of the present invention E.

Next, a result of comparing the penetration resistance of the knife A according to the present invention and the penetration resistance of a knife according to a comparative example is described. FIG. 3 is plan views of knives of comparative examples A to D, F and G and the knife of the present invention E. FIG. 4 is views illustrating measured values of the penetration resistance by the knives of the comparative examples A to D, F and G and the knife of the present invention E.

Meanwhile, an experiment to measure the penetration resistance was performed by allowing the knife to be tested to vertically penetrate the sclera of a swine eye cut to have a thickness of 400 µm to 450 µm as a material to be penetrated and measuring the resistance by a load cell. The penetration was performed three times for each of three tests.

In FIGS. 3 and 4, in the knife of the comparative example A, the edge in a gradual curved-line shape is formed from the sharp tip through the maximum-width part to the shank part side.

In the knife of the comparative example A, the penetration resistance when forming the initial incision to the material to be penetrated is within a range from approximately 160 mN (millinewton, the same shall apply hereinafter) to approximately 95 mN. Also, the penetration resistance relatively monotonously decreases after forming the initial incision and drastically decreases just before a lapse of 2 seconds (time at which the maximum-width part passes through the material to be penetrated). In this case, since the penetration resistance is small, it may be said that this has the excellent incision performance.

In the knife of the comparative example A, the tip is sharp and the edge is formed through the maximum-width part to the shank part side, so that the penetration resistance is small and this has the excellent incision performance. However, variation in measured values is large, the penetration resistance monotonously decreases, and a change rate is large. Therefore, it might be difficult for the doctor to clearly recognize a time point at which the maximum-width part passes through the tissue.

In the knife of the comparative example B, a substantially linear edge is formed from the sharp tip to the maximum-width part, the edge is not formed from the maximum-width part to the shank part side, and the width dimension linearly decreases.

In the knife of the comparative example B, the penetration resistance when forming the initial incision to the material to be penetrated is within a range from approximately 300 mN to approximately 190 mN. The penetration resistance drastically decreases after forming the initial incision to be maintained at a substantially constant value and drastically decreases just before the lapse of 2 seconds. Especially, the substantially constant penetration resistance when penetrating the material to be penetrated is within a range from approximately 220 mN to approximately 140 mN.

In the knife of the comparative example B, the penetration resistance is large, and the incision performance thereof is poor. Also, the change in the penetration resistance just before the lapse of 2 seconds is large and it might be difficult for the doctor to recognize that the maximum-width part of the knife passes through the tissue when incising the same.

In the knife of the comparative example C, the edge in the gradual curved-line shape is formed from the sharp tip to the maximum-width part, the edge is not formed from the maximum-width part to the shank part and the width linearly decreases.

In the knife of the comparative example C, the penetration resistance when forming the initial incision to the material to be penetrated is within a range from approximately 210 mN to approximately 110 mN. The change in the penetration resistance gradually decreases after forming the initial incision and relatively drastically decreases just before the lapse of 2 seconds.

In the knife of the comparative example C, the penetration resistance is not especially large but is not a small value. Also, the change just before the lapse of 2 seconds is large. Therefore, it might be difficult for the doctor to recognize that the maximum-width part of the knife passes.

In the knife of the comparative example D, the edge is substantially linearly formed from the sharp tip to the maximum-width part, the width gradually decreases from the maximum-width part to the shank part, and thereafter, the width decreases in a curved-line shape convex inward.

In the knife of the comparative example D, the penetration resistance when forming the initial incision to the material to be penetrated is within a range from approximately 180 m to approximately 120 mN. The change in the penetration resistance is small and after forming the initial incision to the tissue, the penetration resistance is substantially constant and drastically decreases just before the lapse of 2 seconds.

In the knife of the comparative example D, the penetration resistance is not especially large but is not a small value. Especially, since the penetration resistance after forming the initial incision to the material to be penetrated is substantially constant, the change just before the lapse of 2 seconds is extremely large. Therefore, it might be difficult for the doctor to recognize that the maximum-width part of the knife passes.

The knife A according to the present invention is illustrated in E. In this knife A, the penetration resistance when forming the initial incision to the material to be penetrated is within a range from approximately 100 mN to approximately 60 mN. Also, after forming the initial incision, the penetration resistance slightly decreases but the change is not large. This relatively gradually decreases just before the lapse of 2 seconds.

In the knife A according to the present invention (E), the penetration resistance is small, the change after forming the initial incision is small, and further, the change just before the lapse of 2 seconds is gradual. Therefore, the doctor may decrease the force when allowing the knife to pass through the tissue, and it is also possible to make an incision by applying constant force. Further, the change in the penetration resistance when the maximum-width part passes through the tissue also is gradual and the doctor may easily recognize that the maximum-width part of the knife passes through the tissue.

The knife of the comparative example F has a shape substantially identical to that of the knife of the comparative example D. That is to say, the knife of the comparative example F is such that the edge is substantially linearly formed from the sharp tip to the maximum-width part, the width gradually decreases from the maximum-width part to the shank part, and thereafter, the width decreases in the curved-line shape convex inward.

In the knife of the comparative example F, the penetration resistance when forming the initial incision to the material to be penetrated is within a range from approximately 160 mN to approximately 130 mN. The change in the penetration resistance is small, the penetration resistance further increases after forming the initial incision to the tissue and drastically decreases just before the lapse of 2 seconds.

In the knife of the comparative example F, the penetration resistance is not especially large but is not a small value. Especially, after forming the initial incision to the material to be penetrated, the penetration resistance increases and the change just before the lapse of 2 seconds is extremely large. Therefore, it might be difficult for the doctor to recognize that the maximum-width part of the knife passes.

In the knife of the comparative example G, the edge is substantially linearly formed from the sharp tip to the maximum-width part, a length of the maximum-width part is substantially identical to the length of the cutting part, the width slightly decreases at the part toward the shank part, and thereafter, the width decreases in the curved-line shape convex inward.

In the knife of the comparative example G, the penetration resistance when forming the initial incision to the material to be penetrated is within a range from approximately 270 mN to approximately 170 mN. The penetration resistance further increases after forming the initial incision to the tissue and drastically decreases just before the lapse of 2 seconds.

In the knife of the comparative example G, the penetration resistance is especially large. Also, after forming the initial incision to the material to be penetrated, the penetration resistance increases and the change just before the lapse of 2 seconds is extremely large. Therefore, a load when the doctor handles is large and it might be difficult to recognize that the maximum-width part of the knife passes.

As in the above-described experimental result, in the knife A of the present invention, a value of the largest penetration resistance generated when forming the initial incision to the material to be penetrated is 100 mN and is the smallest as compared to that of other comparative examples. Therefore, the knife A of the present invention is most excellent in the penetration performance.

They are the knives of the comparative examples A and C and the knife A of the present invention in which the change of the penetration resistance just before the lapse of 2 seconds is small (inclination of a change curve is gradual), and among others, the change in the knife A of the present invention is the smallest. Therefore, in the knife A of the present invention, when the doctor handles the same by applying substantially identical force, even when the maximum-width part of the knife A passes through the tissue, excessive force is not applied to the tissue and there is no possibility of forming an excessive incision.

As described above, in the knife A of the present invention, the penetration resistance when forming the initial incision is small, the change in the penetration resistance after forming the initial incision until the maximum-width part passes therethrough is small, and further, the penetration resistance is present also after the maximum-width part passes. Therefore, the doctor may allow the knife to pass through the tissue by applying small force and may incise the tissue by substantially identical force. Then, since the change in the penetration resistance is small also before and after the maximum-width part passes through the tissue, there is a little possibility of incising the tissue excessively also when the doctor handles by applying the substantially identical force.

INDUSTRIAL APPLICABILITY

The knife according to the present invention has no possibility of forming the excessive incision to the tissue when penetrating the tissue to incise. Therefore, this may be utilized not only to an operation on eye but also to an operation to make an incision while maintaining the dimension of the incision constant.

While this invention has been described as having a preferred design, it is understood that it is capable of further modifications, and, uses and/or adaptations of the invention and following in general the principle of the invention and including such departures from the present disclosure as come within the known or customary practice in the art to which the invention pertains, and as may be applied to the central features hereinbefore set forth, and fall within the scope of the invention.

What is claimed is:

1. A medical knife, comprising:
   a sharp tip;
   a cutting part including a first oblique face formed along an outer periphery, an edge formed by the first oblique face, and a second oblique face formed inside the first oblique face,
   a maximum-width part formed continuously and proximally from the cutting part; and
   a shank part formed continuously and proximally from the maximum-width part,
   wherein a planar projection shape of the cutting part is formed such that a width dimension increases from a side of the sharp tip toward the maximum-width part,
   wherein the first oblique face is formed on an outer peripheral side of the second oblique face on a portion from the cutting part through the maximum-width part to the shank part and the first oblique face extends further toward a side of the shank part than the second oblique face on at least a part of portion from the maximum-width part to the shank part side, and
   wherein a substantially triangular wedge-shaped surface is formed on a side surface of the maximum-width part of a side of the medical knife such that an area of the substantially triangular wedge-shaped surface increases from the cutting part to the shank,
   wherein the cutting part includes a lower oblique face formed on a lower side of the first oblique face, and the edge is formed by the first oblique face formed on an upper side and the lower oblique face formed on the lower side intersecting with each other along the outer periphery forming an intersection,
   wherein the substantially triangular wedge-shaped surface is defined by the edge of the first oblique face and an edge of a lower oblique face, wherein the intersection of the edges defines an apex,
   wherein the first oblique face is formed such that the first oblique face lies on the second oblique face at least at a part of the portion from the maximum-width part to the shank part side, and
   wherein the apex of the substantially triangular wedge-shaped surface is located at a position different from that of the sharp tip of the medical knife.

2. The medical knife according to claim 1,
   wherein the first oblique face and the lower oblique face are formed as ground surfaces of which smoothness is higher than the smoothness of the second oblique face.

3. The medical knife according to claim 1,
   wherein the apex of the substantially triangular wedge-shaped surface is located on the side surface of the maximum-width part of the medical knife.

4. The medical knife according to claim 1,
   wherein the entirety of the substantially triangular wedge-shaped surface is located on the side surface of the maximum-width part of the medical knife.

* * * * *